(12) United States Patent
Slemker

(10) Patent No.: US 7,344,567 B2
(45) Date of Patent: Mar. 18, 2008

(54) IMMEDIATE POSTOPERATIVE PROSTHESIS

(75) Inventor: Tracy C. Slemker, Clayton, OH (US)

(73) Assignee: Prosthetic Design, Inc., Clayton, OH (US)

( * ) Notice: Subject to any disclaimer, the term of this patent is extended or adjusted under 35 U.S.C. 154(b) by 199 days.

(21) Appl. No.: 11/186,418

(22) Filed: Jul. 21, 2005

(65) Prior Publication Data

US 2006/0020349 A1    Jan. 26, 2006

Related U.S. Application Data

(60) Provisional application No. 60/590,057, filed on Jul. 21, 2004.

(51) Int. Cl.
*A61F 2/60* (2006.01)
*A61F 2/78* (2006.01)

(52) U.S. Cl. ...................................................... 623/33

(58) Field of Classification Search ............ 623/32–37
See application file for complete search history.

(56) References Cited

U.S. PATENT DOCUMENTS 4,459,709 A * 7/1984 Leal et al. ................... 156/60

| | | |
|---|---|---|
| 5,163,965 A | 11/1992 | Rasmusson et al. |
| 5,211,667 A | 5/1993 | Danforth |
| 5,651,792 A | 7/1997 | Telikicherla |
| 5,728,165 A | 3/1998 | Brown, Sr. |

OTHER PUBLICATIONS

Fillauer, Inc., Post-Op Adapter Component Parts, Fillauer, Inc., Chattanooga, TN., U.S.A.
Becker Orthopedic, Post-Op Model P403010, Becker Orthopedic, Troy, Michigan, U.S.A.
Otto Bock, Models 4R26 & 4R28, Otto Bock, Minneapolis, MN., U.S.A.

* cited by examiner

*Primary Examiner*—Bruce Snow
(74) *Attorney, Agent, or Firm*—Taft Stettinius & Hollister LLP

(57) ABSTRACT

An immediate postoperative prosthesis including: a base adapted to receive a distal prosthetic component, the base comprising a substantially circular pan having a raised wall extending proximally about its periphery; a plurality of flexible straps mounted to and extending proximally from the interior face of the raised wall of the circular pan, the flexible straps adapted to interface with a postoperative residual limb; and wrap materials wrapped around and substantially solidified about the flexible straps. The invention also includes a process for postoperative fitting of a prosthetic component to a residual limb of a prosthetic recipient.

13 Claims, 2 Drawing Sheets

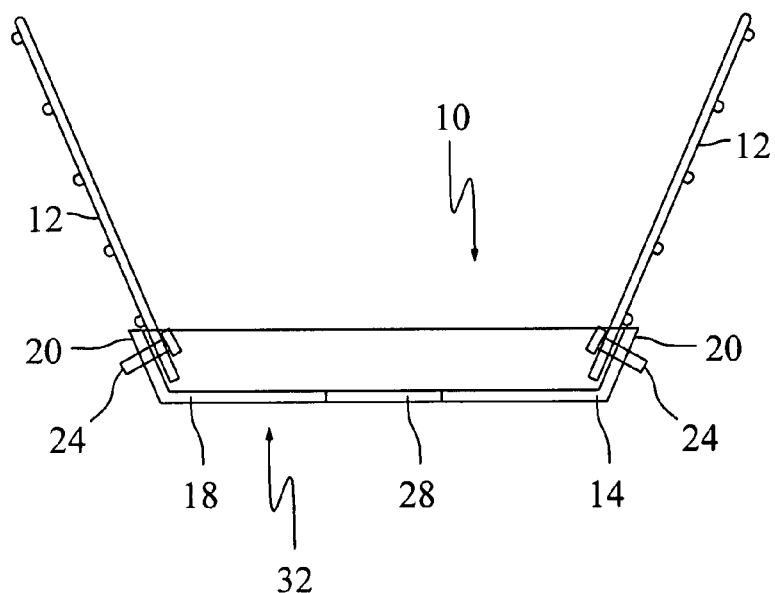
FIG. 2
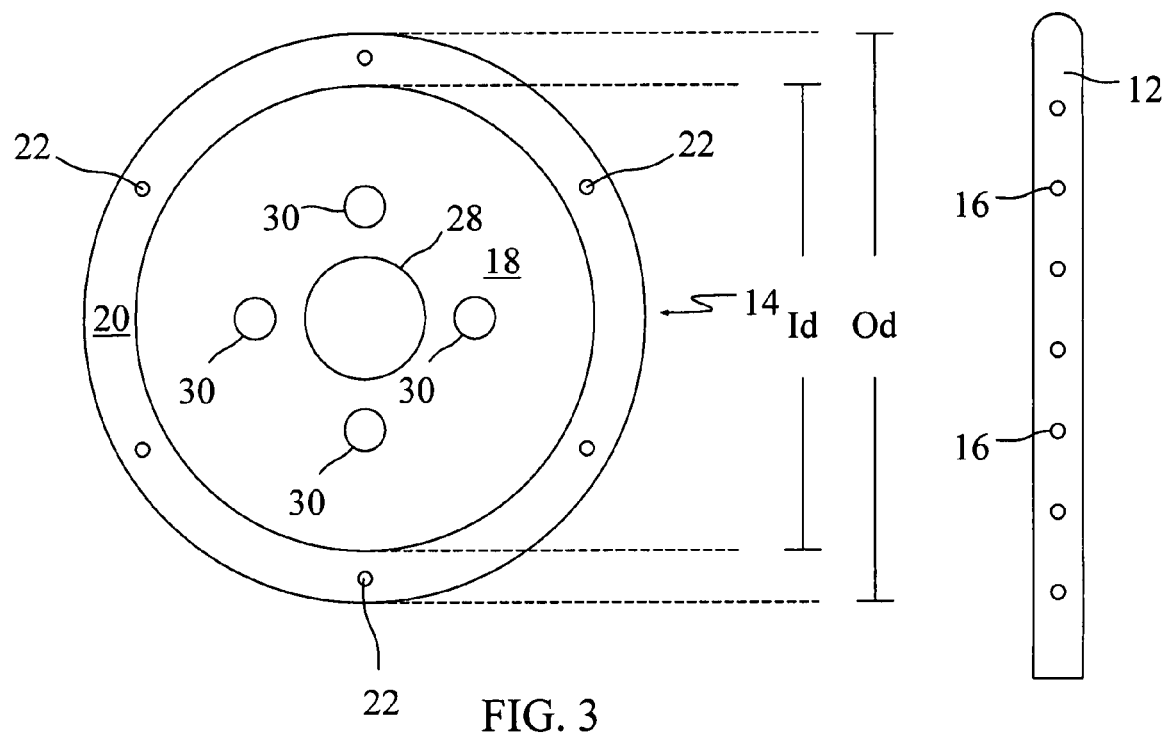
FIG. 3
FIG. 4

IMMEDIATE POSTOPERATIVE PROSTHESIS

CROSS-REFERENCE TO RELATED APPLICATIONS

This application claims the benefit of U.S. Provisional Patent Application Ser. No. 60/590,057, entitled "IMMEDIATE POSTOPERATIVE PROSTHESIS," filed on Jul. 21, 2004, the disclosures of which are incorporated herein by reference.

BACKGROUND OF THE INVENTION

The prior art contains various devices and methods for joining a prosthetic limb to an amputee's residual limb. However, most of these devices and methods require a significant amount of time to be fabricated or implemented. Accordingly, there is a need for an immediate postoperative prosthesis that can be fitted to an amputee's residual limb substantially immediately after an amputation procedure. The present invention addresses this need.

SUMMARY OF THE INVENTION

The present invention is directed to prosthetic devices and, more specifically, to postoperative prosthetic devices and methods of utilizing postoperative prosthetic devices substantially immediately after an amputation procedure. The invention includes a prosthetic frame that comprises a distal attachment plate with straps extending proximally therefrom. The frame is adapted to be positioned on the patient's residual limb and wrapped with bandages or other wrappings having embedded plaster or fiberglass resin that cure about the frame to form a socket. The socket is adapted to receive a patient's residual limb therein to mount the limb to one or more prosthetic components.

Accordingly, it is a first aspect of the present invention to provide an immediate postoperative prosthesis including: a base adapted to receive a distal prosthetic component, the base comprising a substantially circular pan having a raised wall extending proximally about its periphery; a plurality of flexible straps mounted to and extending proximally from the interior face of the raised wall of the circular pan, the flexible straps adapted to interface with a postoperative residual limb; and wrap materials wrapped around and substantially solidified about the flexible straps.

In a further detailed embodiment, the immediate postoperative prosthesis includes a coupling mechanism associated with the frame that is adapted to receive a standard prosthetic pyramid or any other prosthetic limb coupling component. The prosthetic coupling may be used to mount the temporary socket to a prosthetic knee joint, prosthetic pylons, and a prosthetic foot coupled thereto for use by above the knee amputees, for example.

It is a second aspect of the present invention to provide a process for postoperative fitting of a prosthetic component to a residual limb of a prosthetic recipient, the process including the steps of: (a) fitting an immediate postoperative prosthesis frame component to a patient's residual limb, the immediate postoperative prosthesis frame component including a circular pan having a raised wall extending proximally about the pan's periphery, and having at least four straps mounted thereto and extending proximally therefrom, wherein the circular pan receives a distal end of the residual limb, and wherein each flexible strap extends proximally along the residual limb; (b) wrapping wrap materials about the flexible straps; and (c) allowing the wrap materials to harden about the flexible straps.

BRIEF DESCRIPTION OF THE DRAWINGS

FIG. 2 is a cross-sectional view of the exemplary embodiment of FIG. 1;

FIG. 3 is an overhead view of an exemplary base plate for use with the exemplary embodiment of FIG. 1; and FIG. 4 is frontal view of an exemplary strap for use with the exemplary embodiment of FIG. 1.

DETAILED DESCRIPTION

Figure 1:
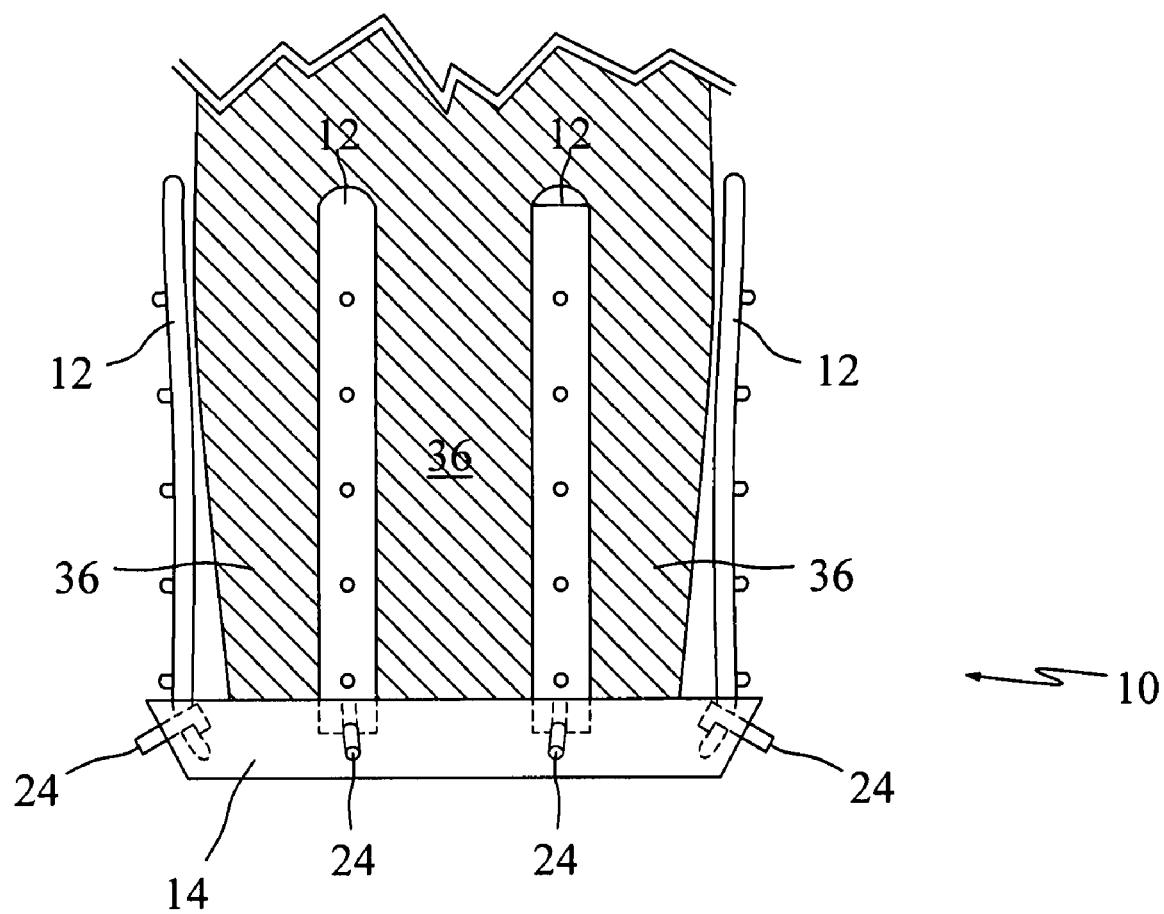
FIG. 1 is an exemplary embodiment of a prosthetic frame for a postoperative prosthetic socket in accordance with the present invention positioned on a residual limb.

Referencing FIGS. 1-4, an exemplary embodiment of an immediate postoperative prosthesis (IPOP) frame 10 may include one or more substantially flexible straps 12 mounted to a base 14 so as to extend upward in a proximal direction with respect to the base 14. The straps 12, in an exemplary embodiment, comprise eighteen gauge stainless steel alloy (304) having a length of 7.5 inches and a width of 0.625 inches. Each strap 12 may include one or more eyelets 16 therethrough to facilitate mounting the straps 12 to the base 14 using fasteners 24.

The base 14 may comprise a circular pan 18 having an angled raised wall 20 that projects circumferentially outward from the flat bottom of the pan. An exemplary internal diameter Id of the circular pan may be 3.625 inches, with an exemplary outer diameter Od of the raised wall being 4.375 inches, and the angled wall 20 having a height of 0.625 inches. The wall 20 may include holes 22 therethrough that are adapted to receive fasteners 24 for mounting the straps 12 to the base 14. In exemplary form, the IPOP frame 10 includes at least four straps 12 (in an exemplary embodiment, six straps are used) circumferentially mounted in an equidistant manner to the base 14 using a 0.125 inch pop rivet 24 having a length of 0.5 inches.

The pan 18 can also include a center hole 28 extending through the flat bottom, and a series of smaller holes 30 arranged in a standard 4-hole pattern around the center hole 28. The smaller holes 30 are adapted to receive fasteners for mounting a prosthetic coupling such as a pyramid (not shown) to the distal side 32 of the IPOP frame 10. In an exemplary form, the four holes 30 are circumferentially distributed about the center hole 28 in ninety degree increments.

Referencing FIG. 1, the exemplary IPOP frame 10 may be utilized to construct a temporary plaster or fiberglass prosthetic outer socket for an amputee substantially immediately after an amputation procedure. Following an amputation procedure, the residual limb 36 will typically be swollen as a result of inflammation and include bandages wrapped therearound. The swelling along with the wrappings of bandages distorts the true dimensions of the residual limb 36 such that final fitting to a permanent prosthetic socket is impractical. Nevertheless, the amputee may want to utilize the residual limb 36 while it is healing in a weight bearing capacity. This requires fabrication of a temporary prosthetic socket to interface with endoskeletal prosthetic components (such as a prosthetic knee-frame, pylon, and foot) to simulate natural load bearing tissue.

To fabricate the outer socket, the pan 18 is positioned adjacent to the distal end of the residual limb 36, which may include a silicon sock (not shown) rolled thereon to provide an additional layer of padding. The straps 12, being already mounted to the pan 18 by the pop rivets 24, are circumferentially distributed about the limb 36 and are positioned to approximate the exterior features thereof in a linear fashion. Each strap 12 may be creased lengthwise to provide a V-shaped strap having a convex/concave shape where the convex side faces outwardly. In still a further detailed exemplary embodiment, each strap 12 may be machined to include punched through projections or teeth (not shown) on their outward-facing surfaces to facilitate gripping to wrapping materials that will be wrapped thereover. After the pan 18 and straps 12 are in position, wraps (not shown) can be applied over the straps 12 and the wall 20 of the base 14 to mount the IPOP frame 10 to the residual limb.

It is also within the scope and spirit of the present invention for the straps 12 to be creased in a U-shaped manner, where the concave portion of the strap 12 faces the residual limb, while the convex portion of the strap faces away from the residual limb. The U-shaped straps 12 may include a series of teeth machined from a stamping operation or other similar procedure to increase the gripping ability of the straps 12, over which the wraps are received.

In either instance, the ends of the straps 12 and any teeth provide points where the straps 12 are adapted to grip the wraps. The wraps may include uncured plaster, fiberglass resin, or some other composition that will cure to provide a temporary socket for the amputee. In an exemplary instance, the wraps comprise fabric bands soaked in a resin that are circumferentially wound around the straps 12 and become embedded therein. As the resin cures, the bands, resin, and IPOP frame 10 become integrated together to comprise a substantially rigid shell of a temporary prosthetic socket.

To apply the wrap after skin closure bandage and compression socks have been applied to the residual limb 36, the following procedure can be followed. At room temperature, a plaster bandage or synthetic resin impregnated bandage is dipped into tepid water and squeezed of excess water. A layer of the material is then wrapped in place as a base to receive the base 14 to fit securely to the residual limb. The bandage material is then wrapped over the wall 20 of the base 14 and the distal portion including the rivet heads to sandwich and mechanically lock the part in place. The wall 20 is also placed in a position so the practitioner can easily bi-valve, or cut the cast down along both sides and in the distal front to access the limb while allowing the option of reapplying the same cast when hardened. This application process takes approximately ten minutes, after which the material takes approximately ten minutes to initially cure when the procedure is performed at room temperature (approximately 20° C.).

Following from the above description and invention summaries, it should be apparent to those of ordinary skill in the art that, while the methods and apparatuses herein described constitute exemplary embodiments of the present invention, it is to be understood that the inventions contained herein are not limited to the above precise embodiment and that changes may be made without departing from the scope of the invention as defined by the following proposed points of novelty. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

I claim:

1. An immediate postoperative prosthesis comprising:
a base adapted to receive a distal prosthetic component, the base comprising a substantially circular pan having a raised wall extending proximally about its periphery;
a plurality of flexible straps mounted to and extending proximally from the raised wall of the circular pan, the flexible straps adapted to interface with a postoperative residual limb; and
wrap materials wrapped around and substantially solidified about the flexible straps;
wherein the flexible straps comprise a plurality of teeth on an outer surface thereof for improving the grip of the flexible straps to the wrap materials.

2. An immediate postoperative prosthesis comprising:
a base adapted to receive a distal prosthetic component, the base comprising a substantially circular pan having a raised wall extending proximally about its periphery;
at least four flexible straps mounted to and extending proximally from the raised wall of the circular pan, the flexible straps adapted to interface with a postoperative residual limb socket; and
wrap materials wrapped around and substantially solidified about the flexible straps;
the raised wall of the circular pan includes a plurality of holes therethrough adapted to receive a fastener therethrough;
each flexible strap has one or more holes therethrough for coupling each flexible strap to a respective hole in the raised wall of the circular pan according to the length at which each flexible strap is to extend from the base; and
a plurality of fasteners couples each flexible strap to the respective hole in the raised wall of the circular pan, each fastener being substantially flush with the flexible strap and each strap extending beyond the proximal edge of the raised wall such that they provide a frame for the wrap materials.

3. The immediate postoperative prosthesis component of claim 2, wherein the flexible straps are longitudinally creased, wherein the concave side of each flexible strap faces inwardly.

4. The immediate postoperative prosthesis component of claim 2, wherein:
the circular pan comprises a central hole extending therethrough and a plurality of complimentary openings distributed thereabout and extending therethrough, the plurality of openings being adapted to couple to a mounting component from a prosthetic device; and
the raised wall of the circular pan extends at a radially outward angle from the periphery of the circular pan.

5. An immediate postoperative prosthesis comprising:
a base adapted to receive a distal prosthetic component, the base comprising a substantially circular pan having a raised wall extending proximally about its periphery;
at least four flexible straps mounted to and extending proximally from the raised wall of the circular pan, the flexible straps adapted to interface with a postoperative residual limb socket; and
wrap materials wrapped around and substantially solidified about the flexible straps;
the circular pan comprises a central hole extending therethrough and a plurality of complimentary openings distributed thereabout and extending therethrough, the plurality of openings being adapted to couple to a mounting component from a prosthetic device;

the raised wall of the circular pan extends at a radially outward angle from the periphery of the circular pan;

the raised wall of the circular pan includes a plurality of holes adapted to receive a fastener therethrough;

each flexible strap has one or more holes therethrough for adjustably coupling each flexible strap to the raised wall of the circular pan according to the length at which each flexible strap is to extend from the base, each flexible strap being adapted to interface with a postoperative residual limb; and a plurality of fasteners couples each flexible strap to the raised wall of the circular pan, each fastener being substantially flush with the flexible strap and extending beyond the exterior face of the raised wall such that they interface with the wrap materials.

6. The immediate postoperative prosthesis component of claim 5, wherein the flexible straps comprise a plurality of teeth for improving the grip of the flexible straps to the wrap materials.

7. The immediate postoperative prosthesis component of claim 2, wherein the flexible straps comprise a plurality of teeth on an outer surface thereof for improving the grip of the flexible straps to the wrap materials.

8. The immediate postoperative prosthesis component of claim 7, wherein the flexible straps are formed from eighteen gauge stainless steel.

9. The immediate postoperative prosthesis component of claim 2, wherein the flexible straps are longitudinally creased, wherein the concave side of each flexible strap faces inwardly.

10. The immediate postoperative prosthesis component of claim 9, wherein the flexible straps comprise a plurality of teeth on a convex side thereof for improving the grip of the flexible straps to the wrap materials.

11. The immediate postoperative prosthesis component of claim 10, wherein the wrap materials comprise uncured resin-soaked fabric bands.

12. The immediate postoperative prosthesis component of claim 7, wherein the wrap materials comprise uncured resin-soaked fabric bands.

13. The immediate postoperative prosthesis component of claim 2, wherein the wrap materials comprise uncured resin-soaked fabric bands.

* * * * *